United States Patent
Vilsmeier et al.

(10) Patent No.: US 6,640,128 B2
(45) Date of Patent: Oct. 28, 2003

(54) METHOD AND DEVICE FOR THE NAVIGATION-ASSISTED DENTAL TREATMENT

(75) Inventors: Stefan Vilsmeier, Kufstein (AT); Rainer Birkenbach, Poing (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 0 days.

(21) Appl. No.: 09/834,738

(22) Filed: Apr. 13, 2001

(65) Prior Publication Data

US 2002/0077542 A1 Jun. 20, 2002

(30) Foreign Application Priority Data

Dec. 19, 2000 (EP) .............................. 00127288

(51) Int. Cl.$^7$ ................................. A61B 5/05
(52) U.S. Cl. ................. 600/427; 600/426; 600/414; 433/215
(58) Field of Search ................. 433/215, 213, 433/68–71; 600/427, 411, 414, 426

(56) References Cited

U.S. PATENT DOCUMENTS

| | | | | |
|---|---|---|---|---|
| 5,340,309 A | * | 8/1994 | Robertson | 433/215 |
| 5,545,039 A | * | 8/1996 | Mushabac | 433/215 |
| 5,562,448 A | * | 10/1996 | Mushabac | 433/215 |
| 5,842,858 A | * | 12/1998 | Truppe | 433/215 |
| 5,846,081 A | | 12/1998 | Bushway | |
| 6,227,850 B1 | * | 5/2001 | Chishti et al. | 433/24 |
| 6,285,902 B1 | * | 9/2001 | Kienzle et al. | 600/427 |
| 6,314,312 B1 | * | 11/2001 | Wessels et al. | 600/427 |
| 6,490,467 B1 | * | 12/2002 | Bucholz et al. | 600/407 |

FOREIGN PATENT DOCUMENTS

| | | |
|---|---|---|
| DE | 199 02 273 A | 8/2000 |
| WO | 99/16380 | 4/1999 |

\* cited by examiner

*Primary Examiner*—Gregory L. Huson
*Assistant Examiner*—Amanda Flynn
(74) *Attorney, Agent, or Firm*—Renner, Otto, Boisselle & Sklar, LLP

(57) ABSTRACT

A method for assisting in a dental treatment, wherein: a three-dimensional volume data set for the tooth and/or jaw area of a patient is produced by means of an imaging method, for example tomographic imaging; the tooth and/or jaw area is registered and/or referenced by means of a computer-assisted navigation and/or tracking system using the volume data set; instruments and apparatus for treatment are registered and/or referenced relative to said computer-assisted navigation and/or tracking system, and positionally tracked; and wherein said navigation and/or tracking system supplies information for assisting and/or guiding the treatment before, during or after the treatment, by means of an output unit. It further concerns a device for implementing the method and the application of the device for assisting in a dental treatment.

19 Claims, 1 Drawing Sheet

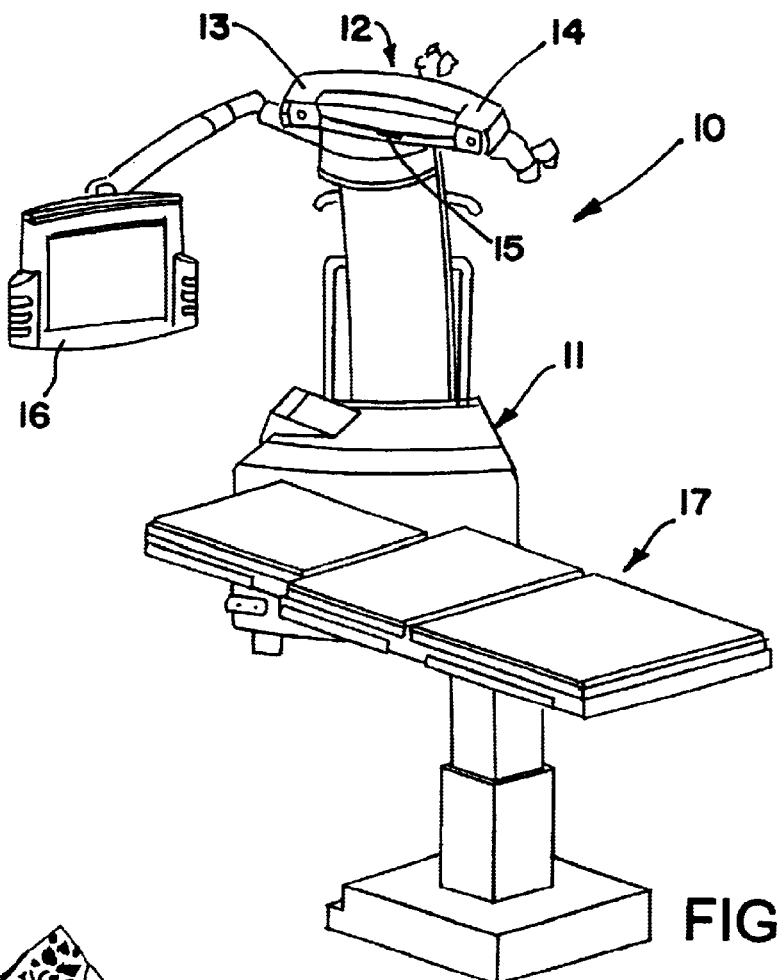
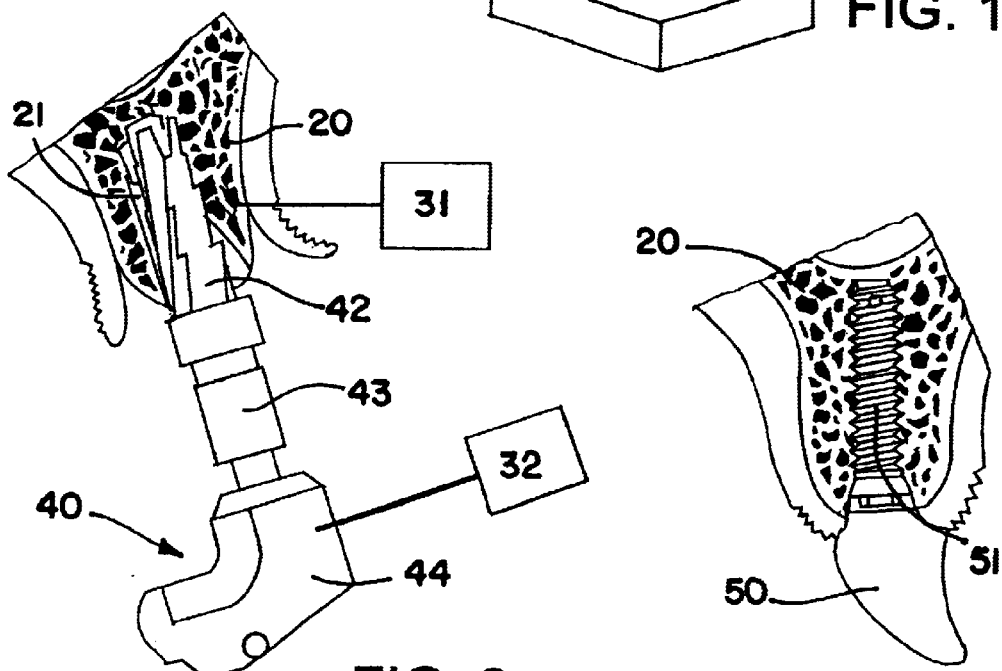
FIG. 1
FIG. 2
FIG. 3

METHOD AND DEVICE FOR THE NAVIGATION-ASSISTED DENTAL TREATMENT

The present invention relates to a method and a device for navigation-assisted dental treatment, in accordance with patent claim 1 as well as the preamble of patent claim 13. It further relates to the application of a device in accordance with the present invention for assisting in a dental treatment.

Dental treatments, in particular invasive dental treatments, are conventionally still mostly carried out to date without the aid of imaging or navigation. When carrying out invasive measures, the dentist mostly relies on what he can see in the patient's mouth and on his own experience. To aid him, especially in the case of orthodontics, x-rays are frequently brought into play.

This approach has a number of basic disadvantages. Inexperienced dentists could, for example when drilling into the jaw to insert an implant adaptor, drill or fraise in an incorrect direction or too far into the jaw, which in the worst case could lead to nerve damage. The x-ray images used are often distorted and thus introduce inaccuracies. The information from the x-ray image is only employed by the physician to note the anatomy, and this too can be a source of errors. The use of drilling templates is expensive and slows treatment.

A method for simplifying a dental diagnosis and treatment is known from U.S. Pat. No. 5,562,448, wherein the surface of a tooth and/or jaw structure is scanned with an instrument, whilst the movement of a second element arranged parallel thereto and performing the same movement, a so-called pantograph arm, is tracked with cameras. For the purposes of diagnosis, the surface of a tooth is covered and captured as data. To further assist, other information from x-ray images is additionally processed and integrated. Multiple and various pantograph units may be employed, and it is foreseen that the device in accordance with U.S. Pat. No. 5,562,448 be used to assist in treatment, and in particular for practice operations.

The fundamental disadvantage of the system described above is that only surface data are available to assist in treatment. The areas to be treated, however, are often in the interior of the tooth and/or jaw bone, respectively. With the method proposed here, it is possible to obtain precise data on such internal structures. This becomes especially evident when an orthodontic treatment is to be carried out in an area where a tooth is missing. The surface of the jaw bone itself may yet indeed be determined as necessary by invasive treatments, but its internal structure and position cannot be ascertained by means of this system. Moreover, preparing a treatment device or scanning device with a parallel pantograph arm attached at a distance by means of an attachment is costly, and a bulky instrument emerges which still has to be fixed to a pivoting arm to be manageable and operative.

It is the object of the present invention to provide a method and a device for navigation-assisted dental treatment which overcomes the aforesaid problems of the prior art. In particular, a sufficiently manageable navigation-assisted dental treatment system is to be proposed, which allows optimally precise treatments and surgery. This object is solved in accordance with the present invention by a method for assisting a dental treatment, wherein:

a three-dimensional volume data set for the tooth and/or jaw area of a patient is produced by means of an imaging method, for example tomographic imaging;
  the tooth and/or jaw area is registered and/or referenced by means of a computer-assisted navigation and/or tracking system using the volume data set;
  instruments and apparatus for treatment are registered and/or referenced relative to the computer-assisted navigation and/or tracking system, and positionally tracked; and wherein:
  the navigation and/or tracking system supplies information for assisting and/or guiding the treatment before, during or after the treatment, by means of an output unit.

The advantage of this invention is based in particular on the provision of a three-dimensional volume data set for the tooth and/or jaw area of a patient. With such information, which may be obtained for example using a tomographic method, the physician carrying out the treatment now no longer has only surface information at his disposal, but also information on the internal structure of tooth and/or jaw, and may carry out the operation on the basis of this information. In this way, it can be ensured that healthy tissue or bone structures can be left largely untouched, while diseased or mutated structures can be completely removed. In the field of dental implantology in particular, the present invention enables drilling or fraising in the wrong direction to be ruled out and, because navigation and/or tracking are always providing information about the position of the drill or fraise tip, it is also possible to actively prevent drilling or fraising either too far or not far enough, such that nerve damage or a poor grip by a tooth implant adaptor can be avoided. In accordance with the present invention, the position of the relevant parts of the patient as well as the position of the instruments is known to the navigation and/or tracking system at all times, and all these data can be outputted to a screen and assist the physician with the treatment. The treatment thus becomes on the whole more precise; when inserting dental implant adaptors, this can extend to setting the dental prosthesis itself directly into a pre-determined position on the adaptor, without the need for ball joints, as hitherto used, for adjustment.

The device in accordance with the present invention comprises a device which produces a three-dimensional volume set for the tooth and/or jaw area of a patient by means of an imaging method, for example tomographic imaging, and registers and/or references the tooth and/or jaw area by means of the navigation and/or tracking system using the volume data set.

Within the framework of the present invention, the position of the instruments or apparatus for treatment is basically tracked by the navigation and/or tracking system. This can be sufficient if the head of the patient is held in place sufficiently and the position of the holding device in relation to the navigation and/or tracking system has been established. This applies in particular to treatment in the upper jaw area. Essentially, however, there also exists the possibility of positionally tracking the tooth and/or jaw area using the navigation and/or tracking system, in order to always have current data on the position of the area to be treated available. Such positional tracking of the tooth and/or jaw area is particularly recommendable where the patients are not held in place, or in treatment of the lower jaw.

In a preferred embodiment of the invention, the tooth and/or jaw, as well as the desired positional course of an instrument, planned to begin with or inter-operatively, are displayed on a screen output during treatment, and the actual positional course of the instrument is positionally tracked. When the desired positional course and the actual positional course deviate, a visual and/or acoustic warning signal can be given, so that the physician can make the appropriate corrections. In order to also be able to assist such corrections when deviations between the desired positional course and the actual positional course have been established, a new desired positional course can be calculated and outputted by the computer-controlled navigation and/or tracking system, which the physician can then follow.

Within the framework of the present invention, a navigation and/or tracking system may be used, wherein a data set comprising three-dimensional data of the tooth and jaw area is registered and/or referenced by means of one of the following methods:

referencing and/or registering the data set by means of anatomical landmarks;

referencing and/or registering the data set by means of artificial landmarks, in particular actively emitting or reflecting markers;

referencing and/or registering the data set by means of a surface-matching technology based on anatomical scanning;

referencing and/or registering the data set by means of a surface-matching technique based on non-contact scanning, in particular on generating detectable laser beam markings on the surface of the patient.

Combinations are also possible.

The tooth and/or jaw area can advantageously be positionally tracked by a dynamic tracking method, in particular by a simultaneous dynamic tracking of the upper and/or lower jaw or of the upper jaw and lower jaw individually, preferably using reference adaptors with an arrangement of markers attached thereto.

Known systems may be used as the navigation and/or tracking system, such as for example those already currently used in stereotaxy. For example, there is an optical navigation and/or tracking system available, which registers and/or references and positionally tracks the tooth and/or jaw area and/or the instruments or apparatus for treatment, using markers or arrangements of markers and a camera system. An infrared navigation and/or tracking system in which the markers are formed as reflectors is also particularly suitable as the optical system. The option likewise exists, within the framework of the invention, of using a magnetic field based navigation and tracking system which registers and/or references and positionally tracks the tooth and/or jaw area and/or the instruments or apparatus for treatment, using an external magnetic field and induction-sensitive elements.

As already mentioned above, combinations of these navigation and tracking systems may be used which are adjusted to each another. An optical navigation and tracking system is thus used in accordance with an advantageous embodiment of the invention, which registers and/or references and positionally tracks the tooth and/or jaw area. Additionally in this embodiment, a magnetic field based navigation and tracking system is used, which is coupled to it with respect to navigation and/or tracking, and which registers and/or references and positionally tracks the instruments or apparatus for treatment, using an external magnetic field and induction-sensitive elements.

The three-dimensional volume data set, on the basis of which the treatment takes place, may be obtained for example by computer tomography, nuclear spin tomography, PET, SPECT, ultrasonic imaging and similar methods, and by a combination of such methods. If the treatment is additionally assisted by intra-operative imaging methods, the possibility emerges of taking structural changes caused by the surgery into account in the navigation, even during the treatment. This is particularly advantageous when the patient's mouth is being held open and there is then no option of testing the state of biting by the patient actually closing his/her jaw. The system, which knows the present actual status of the patient from the intra-operative imaging methods, can for example simulate the closing of the jaw virtually, and display necessary post-operative treatment, without the patient having to be released from the holding position.

The screen output in accordance with the invention may be represented in one of the following forms:

a two and three-dimensional representation of the registered and/or referenced and positionally determined tooth and/or jaw area, and of the instruments with desired and actual positional courses (two-dimensional only, three-dimensional only, or even a combined representation may be selected);

OPG views;

digitally reconstructed radiographs (DRRs), in particular in the form of OPG views.

The present invention also takes into consideration the use of robot technology. The treatment may accordingly be carried out by instruments which are fully or partly guided by a robot, which is registered and/or referenced in the navigation and/or tracking system and positionally tracked, and which is controlled by the system. Within this framework, it is possible, for example, to position a drill or a fraise above a defined point in the jaw bone using a robot arm. Drilling or fraising may then also be completed by the robot, or alternatively by the physician guiding the instrument on the robot arm, the robot allowing correct movements and preventing incorrect movements.

The device in accordance with the invention and its embodiments are described in the claims. The advantages mentioned above may similarly be achieved with this device.

Furthermore, the invention concerns the use of such a device for assisting in a dental treatment.

The invention is described in the following in more detail, on the basis of an example embodiment and the enclosed drawings, in which:

FIG. 1 is a navigation and tracking system which may be used within the framework of the present invention;

FIG. 2 is a navigated and/or tracked fraise drilling into a jaw bone; and

FIG. 3 is an inserted tooth implant.

FIG. 1 shows a navigation and/or tracking system, as may be used within the framework of the present invention for assisting in a dental treatment. The system as a whole is designated the reference number 10, and comprises a patient's table 17 on which a patient may be positioned for treatment. Instead of the patient's table 17, a dentist's chair could, for example, also be used.

The system further comprises a portable device, at the base of which a computer 11 is situated, which takes on all the controlling and setting, as well as the processing of received signals and signals to be outputted. A camera support 12, which is attached to an arm of the system, comprises two infrared cameras 13 and 14, as well as an infrared transmitter 15. With these cameras, markers or arrangements of markers attached to the patient and/or to various instruments or apparatus for treatment may be tracked and positionally referenced and/or registered. These are preferably arrangements of reflecting markers, wherein determining their position may also be used to detect, for example, the position of the tip of an instrument.

A screen 16 is provided as the output device, which makes a series of two or three-dimensional views of the current instrument positions and anatomical data available to the physician. Desired and actual positional courses for the instruments may simultaneously be inserted. The screen can also serve as an input medium, for example for setting the desired views. Moreover, the system can also supply acoustic signals, for example when the calculated optimal drilling channel and the actual drilling channel of a jaw drill deviate.

The present invention is particularly suitable for measures carried out of orthodontic treatment, and here specifically within the framework of dental implantology.

FIG. 2 shows an anchoring hole 21 being fraised out in a jaw bone 20 by a fraise 42 fixed to its mounting 41 via an adaptor 43. For this purpose, the mucous membrane over the jaw bone is removed.

It is already clear from FIG. 2 that the hole 21 in the jaw bone 20 must have a precisely defined course, if only so that enough jaw bone remains on each side surrounding the hole 21. For, as can be seen in FIG. 3, a tooth implant adaptor 51 is later inserted into the hole, which the tooth implant 50 is to be placed upon. This tooth implant 50, however, has to be positioned with sufficient stability, and in particular should fit in with the alignment of the adjacent teeth. The alignment of the hole 21 (FIG. 2) must also therefore be carried out with the utmost precision.

This precision may now be achieved with the aid of the present invention. For this purpose, both the jaw bone 20 and the fraising device, designated as a whole by the reference number 40, are referenced and/or registered and positionally tracked in a navigation and/or tracking system 10. With the jaw, this takes place via a marking 31 firmly attached to the jaw, and with the fraising device via a marking 32 fly attached thereto. Using these markings, whose position is constantly detectable in the navigation system 10, the current positions of the jaw anatomy and of the instrument 40 and its fraise tip 42 are known at all times. In accordance with the invention, all the surface data as well as all the internal data of the jaw area are known from the three-dimensional volume data acquisition, and in this way operations may be planned, monitored and guided which take into account all the external and internal circumstances of the patient's physical structure.

The markings 31 and 32 can be of different types. An arrangement of reference markers clipped to the jaw, for example, is suitable for the marking 31. Such a reference adaptor comprises, for instance, three markers and can communicate the position of the part of the body to which it is attached to the navigation system 10 at any time.

Marking 32 may similarly comprise such an arrangement of markers attached to the instrument, wherein it is easily possible, for instance, to attach the arrangement of markers to the rear end of the fraising device 40 via an adaptor, in order that it does not interfere with the treatment. It is also the case here that the position of the fraising device 40, and in particular of the tip of the fraise, is known at all times, and can be used within the framework of monitoring or guiding the treatment.

Instead of arrangements of markers, other known tracking systems may also be used, for example magnet-based systems in which a magnetic field is generated in the treatment area and induction-sensitive elements, for instance coils, are positioned in or on the instruments or on the patient. Accordingly, markings 31 and 32 can also stand for such magnet tracking elements, which are also suitably arranged in the instrument housings. Various systems may be used in this respect, such as those which use pulsed, direct current induced magnetic fields, those which use alternating current fields, those which use completely passive receivers and those which use active receivers. A major advantage of these magnet-based navigation and tracking systems is that no line of sight between markers 31 and 32 and a camera system need exist, which gives the physician significant freedom of movement.

A treatment, for example the insertion of a dental implant, is carried out for example as follows. Firstly, a tomographic image is produced for the tooth and/or jaw area of a patient, i.e. a three-dimensional volume data set, in which all the information about the treatment area is stored. These data are then communicated to the navigation and/or tracking system 10, i.e. stored in the computer 11, and via a marking 31 the system 10 detects the current position of all structural data during the treatment, also therefore internal structural data of the tooth and/or jaw area of the patient. The physician can now input, for example on a touch-sensitive screen 16, where approximately he wishes to insert the drill hole for the implant adaptor 51, wherein this step can also be performed before the treatment. On the basis of all the available data, including data on various standard implants (and in particular the implant to be used), the system calculates exactly how the hole to be drilled should run and where it should end. This drilling line can then be virtually represented on the screen 16 in a number of views (two or three-dimensionally). The physician can now pick up a drill or fraise, whose position in the navigation system is likewise known. In particular, a standard fraise 40 may for example be used, whose position at the tip (and entire external form) is known, and may be tracked in the navigation and/or tracking system via the marking 32. Aided by the screen output, the physician can now drill or fraise on the pre-planned line, and is warned if he deviates from the direction, or drills and/or fraises too deeply. The result is a clean and precisely aligned hole, which the implant adaptor 51 can be precisely inserted into, in order to give the tooth implant 50—to be inserted later—a fully correct positioning.

What is claimed is:

1. A method for assisting in a dental treatment, comprising the steps of:
    producing a three-dimensional volume data set for a tooth and/or jaw area of a patient by means of an imaging method;
    registering and/or referencing the tooth and/or jaw area by means of a computer-assisted navigation and/or tracking system using the volume data set;
    registering and/or referencing at least one instrument and/or apparatus for treatment relative to the computer-assisted navigation and/or tracking system;
    tracking the position of the at least one instrument and/or apparatus; and
    supplying from the navigation and/or tracking system information for assisting and guiding the dental treatment by means of an output unit before, during or after the dental treatment;
    wherein the tooth and/or jaw area, as well as a desired positional course of an instrument planned to begin with or inter-operatively, are displayed during the treatment on a screen while the actual positional course of the instrument is tracked, a visual and/or acoustic warning signal is outputted when the desired positional course and actual positional course of the instrument deviate, and a new desired positional course is calculated and outnutted when the desired positional course and actual positional course of the instrument deviate.

2. The method as set forth in claim 1, wherein the position of the tooth and/or jaw area is also tracked by the navigation and/or tracking system.

3. The method as set forth in claim 1, wherein a navigation and/or tracking system is used which registers and/or references a data set comprising three-dimensional data for the tooth and jaw area, by means of one of the following methods:

referencing and/or registering the data set by means of anatomical landmarks;

referencing and/or registering the data set by means of artificial landmarks;

referencing and/or registering the data set by means of a surface-matching technology based on anatomical scanning;

referencing and/or registering the data set by means of a surface-matching technique based on non-contact scanning.

4. The method as set forth in claim 1, wherein the position of the tooth and/or jaw area is tracked using a dynamic tracking method.

5. The method as set forth in claim 1, wherein an optical navigation and/or tracking system is used which registers and/or references and positionally tracks the tooth and/or jaw area and/or the instruments or apparatus for treatment, using markers or arrangements of markers and a camera system.

6. The method as set forth in claim 1, wherein a magnetic field based navigation and/or tracking system is used which registers and/or references and positionally tracks the tooth and/or jaw area and/or the instruments or apparatus for treatment, using an external magnetic field and induction-sensitive elements.

7. The method as set forth in claim 1, wherein an optical navigation and/or tracking system is used which registers and/or references and positionally tracks the tooth and/or jaw area, and wherein a magnetic field based navigation and/or tracking system is used which is coupled to it regarding the navigation and/or tracking, and which registers and/or references and positionally tracks the instruments or apparatus for treatment, using an external magnetic field and induction-sensitive elements.

8. The method as set forth in claim 1, wherein said three-dimensional volume data set is obtained by one or more of the following methods:

computer tomography, nuclear spin tomography, PET, SPECT, ultrasonic imaging.

9. The method as set forth in claim 1, wherein the treatment is further assisted by intra-operative imaging methods.

10. The method as set forth in claim 1, wherein a screen output is provided, on the basis of one or more of the following representations:

a two and three-dimensional representation of the registered and/or referenced and positionally determined tooth and/or jaw area as well as of the instruments including desired and actual positional courses;

OPG views;

digitally reconstructed radiographs (DRRs).

11. The method as set forth in claim 1, wherein the treatment is carried out by instruments which are fully or partly guided by a robot which is registered and/or referenced and positionally tracked in the navigation and/or tracking system, and controlled by the system.

12. A device for assisting in a dental treatment, comprising a navigation and/or tracking system which supplies information for assisting and/or guiding the treatment during the treatment by means of an output unit, also instruments and apparatus for treatment which are registered and/or referenced relative to the computer-assisted navigation and/or tracking system and positionally tracked, characterized by a device producing a three-dimensional volume data set for the tooth and/or jaw area of a patient by means of an imaging method, and registering and/or referencing the tooth and/or jaw area by means of a computer-assisted navigation and/or tracking system which uses the volume data set, and wherein the output unit is a screen display, on which the tooth and/or jaw area, as well as a desired positional course of an instrument planned to begin with or inter-operatively, is displayed during the treatment, while the actual positional course of the instrument is positionally tracked, and further comprising an output device which outputs a visual and/or acoustic warning signal when the desired positional course and the actual positional course of the instrument deviate, whereupon a new desired positional course can be calculated and displayed.

13. The device as set forth in claim 12, characterized in that it comprises a device with which the tooth and/or jaw area is also tracked by said navigation and/or tracking system.

14. The device as set forth in claim 12, characterized in that it comprises an optical navigation and tracking system which registers and/or references and positionally tracks the tooth and/or jaw area and/or the instruments or apparatus for treatment, using markers or arrangements of markers and a camera system.

15. The device as set forth in claim 12, characterized in that it comprises a magnetic field based navigation and tracking system, which registers and/or references and positionally tracks the tooth and/or jaw area and/or the instruments or apparatus for treatment, using an external magnetic field and induction-sensitive elements.

16. The device as set forth in claim 12, characterized in that it comprises an optical navigation and tracking system which registers and/or references and positionally tracks the tooth and/or jaw area, and in that it comprises a magnetic field based navigation and tracking system coupled to it regarding navigation and/or tracking, which registers and/or references and positionally tracks the instruments or apparatus for treatment, using an external magnetic field and induction-sensitive elements.

17. The device as set forth in claim 12, characterized in that it further comprises devices which assist in the treatment with intra-operative imaging methods.

18. The device as set forth in claim 12, characterized in that it comprises a robot which fully or partly guides the instruments during the treatment, is registered and/or referenced in the navigation and/or tracking system and positionally tracked, and is controlled by the system.

19. The application of a device as set forth in claim 12, for assisting in a dental treatment.

* * * * *